| United States Patent [19] | [11] Patent Number: 4,483,694 |
| --- | --- |
| Takamura et al. | [45] Date of Patent: Nov. 20, 1984 |

[54] OXYGEN GAS PERMSELECTIVE MEMBRANE

[75] Inventors: Tsutomu Takamura; Atsuo Imai, both of Yokohama; Nobukazu Suzuki, Tokyo, all of Japan

[73] Assignee: Tokyo Shibaura Denki Kabushiki Kaisha, Kanagawa, Japan

[21] Appl. No.: 475,687

[22] Filed: Mar. 14, 1983

[30] Foreign Application Priority Data

Jun. 24, 1982 [JP] Japan ................................ 57-107631
Sep. 10, 1982 [JP] Japan ................................ 57-156758

[51] Int. Cl.$^3$ ............................................ B01D 53/22
[52] U.S. Cl. ........................................ 55/158; 55/16; 55/68; 427/40; 427/126.4; 428/384
[58] Field of Search .............. 55/16, 68, 158; 427/40, 427/126.3, 126.4, 150; 428/384, 386

[56] References Cited

U.S. PATENT DOCUMENTS

| 3,203,086 | 8/1965 | Eyraud et al. | 55/16 X |
| 3,359,705 | 12/1967 | Mullhaupt | 55/16 |
| 3,509,694 | 5/1970 | Imai et al. | 55/16 |
| 3,941,673 | 3/1976 | Takao et al. | 55/158 X |
| 3,957,534 | 5/1976 | Linkohr et al. | 55/158 X |
| 4,106,920 | 8/1978 | Hughes et al. | 55/158 |
| 4,120,663 | 10/1978 | Fally | 55/158 X |
| 4,175,153 | 11/1979 | Dobo et al. | 55/16 X |
| 4,214,020 | 7/1980 | Ward et al. | 55/158 X |

FOREIGN PATENT DOCUMENTS

| 3280 | 1/1973 | Japan | 55/158 |
| 48-26896 | 8/1973 | Japan . | |
| 54-155431 | 12/1979 | Japan . | |

*Primary Examiner*—Robert Spitzer
*Attorney, Agent, or Firm*—Schwartz, Jeffery, Schwaab, Mack, Blumenthal & Koch

[57] ABSTRACT

There is disclosed an oxygen gas permselective membrane comprising a film of a water-containable or wettable metallic oxide.

The oxygen gas permselective membrane according to this invention, though being very thin, does not allow water vapor and carbon dioxide gas in air to permeate therethrough and has a great function for allowing oxygen gas to selectively permeate therethrough.

13 Claims, No Drawings

OXYGEN GAS PERMSELECTIVE MEMBRANE

BACKGROUND OF THE INVENTION

This invention relates to an oxygen gas permselective membrane which can be effectively used in manufacturing an air electrode for a hydrogen/oxygen fuel cell, a metal/air cell or an oxygen sensor, more specifically to an oxygen gas permselective membrane which permits a heavy-load discharge for a long period of time, even if it is in a thin form, and which is excellent in storage properties.

There have hitherto been used gas diffusion electrodes for air electrodes such as various fuel cells, air-metal cells typically including air/zinc cells, and Galvanic oxygen sensors. In the initial period, a thick porous electrode in which distributed pores have a uniform diameter has been used as the gas diffusion electrode. In recent years, however, there have often been used an electrode having a two-layer structure, which comprises a porous electrode body having an electrochemical reduction function for oxygen gas (a function for ionizing oxygen) and simultaneously having a function as a current collector and a thin water repellent layer deposited integrally on the gas-side surface of the electrode body.

In this case, the electrode body may be formed mainly by incorporating a conductive powder, such as an active carbon powder carrying a nickel tungstate having a low reduction overvoltage to oxygen gas; a tungsten carbide coated with palladium-cobalt; nickel; silver; platinum or palladium, into a porous metallic body, a porous carbon body or a non-woven carbon fabric material, by the use of a binder such as polytetrafluoroethylene.

Further, the aforementioned water repellent layer, which will be deposited integrally on the gas-side surface of the electrode body, is a porous thin membrane that comprises a fluorine-containing resin such as polytetrafluoroethylene, tetrafluoroethylene-hexafluoropropylene copolymer, or ethylene-tetrafluoroethylene copolymer, or a resin such as polypropylene, in a form of a porous material including, for instance, a sintered powder material having a particle size of from 0.2 to 40 $\mu$m; a paper-like nonwoven fabric material prepared by heat treatment of fibers comprising the above resin; a similar woven fabric material; a powder material partially replaced the above resin by a fluorinated graphite; a film material prepared by rolling fine powder together with a pore-increasing agent or a lubricant oil, followed by heat treatment, or a film material prepared by rolling without being followed by heat treatment (Japanese Patent Publication No. 44978/1973).

In the air electrode having such a conventional structure as mentioned above, however, the water repellent layer deposited on the gas-side surface of the electrode body is impervious to a used electrolyte but is not impervious to air and water vapor in air.

For this reason, for example, water vapor in air may permeate the electrode body through the water repellent layer in order to dilute the electrolyte; the water in the electrode is otherwise given off through the water repellent layer in order to concentrate the electrolyte. As a result, the concentration of the electrolyte will fluctuate and it will thus be impossible to maintain a stable electric discharge for a long time.

In the case that carbon dioxide gas in air permeates the electrode body through the water repellent layer and is adsorbed by an active layer (a porous portion of the electrode body) therein, the electrochemical reducing function of the active layer to oxygen gas will be reduced at this position, exerting a bad influence upon a heavy-load discharge. Moreover, when an alkaline electrolyte is used, there will occur phenomena such as change in properties of the electrolyte, reduction in the concentration of the electrolyte and, when a used cathode is zinc, passivation of the zinc cathode. Furthermore, in such a case as mentioned above, a carbonate will be formed in the active layer to close some pores and to thereby decrease the region where an electrochemical reduction is carried out, which fact will lead to hindrance in the heavy-load discharge.

A cell having such a structure above will deteriorate in performance below a certain design standard, when stored for a long period of time or when used for a prolonged period.

In order to overcome such disadvantageous problems, there has been proposed a new-type cell in which a water repellent layer of an air electrode is provided, on the gas side (air side) thereof, with a layer comprising a water-absorbing agent such as calcium chloride or a carbon dioxide gas-absorbing agent such as a hydroxide of an alkaline earth metal (Japanese Patent Publication No. 8411/1973). This type of cell can prevent the above-mentioned disadvantageous problems to some extent, but when the absorbing agent has been saturated with water or carbon dioxide gas after a certain period of time, its function will be lost and its effect can be expected no more. After all, such a suggested cell cannot solve the aforementioned problems basically.

Further, it has been attempted to laminate integrally, on the above-mentioned water repellent layer, an oxygen permselective thin membrane such as a polysiloxane membrane (Japanese Patent Publication No. 26896/1973). However, no sufficiently effective oxygen gas permselective membranes have yet been developed.

SUMMARY OF THE INVENTION

An object of this invention is to provide an oxygen gas permselective membrane which is excellent in the function of allowing oxygen gas to selectively permeate. Therefore, when applied to an air electrode, the oxygen gas permselective membrane according to this invention can prevent water vapor or carbon dioxide gas in air from permeating the air electrode body, and thus permits a heavy-load discharge for a long time, and enables the manufacture of a thin air electrode having excellent storage properties.

With respect to this invention, a first aspect is directed to an oxygen gas permselective membrane comprising a thin layer made of a water-containable or wettable metallic oxide, a second aspect is directed to a composite membrane having a two-layer structure in which a thin layer made of a water-containable or wettable metallic oxide is integrally deposited on either surface of a porous membrane of 0.1 $\mu$m or less in pore size, and a third aspect is directed to a composite membrane having a three-layer structure in which a water repellent layer is integrally interposed between the porous membrane and the thin layer of metallic oxide.

DETAILED DESCRIPTION OF PREFERRED EMBODIMENTS

Now, this invention will be further described in detail as follows:

The water-containable or wettable metallic oxide used in this invention means a material having the ability to adsorb water and having properties for permitting the water adsorbed thereon to exist orienting hydroxyl groups thereof to the surface of the oxide as chemically and physically adsorbed water. In this specification, the water-containable (wettable) properties mean the phenomenon that a metallic oxide exists in combination with water molecules, or in a state having an interaction with water molecules. Examples of the metallic oxides above include stannic oxide ($SnO_2$), zinc oxide (ZnO), aluminum oxide ($Al_2O_3$), magnesium oxide (MgO), calcium oxide (CaO), strontium oxide (SrO), barium oxide (BaO), titanium dioxide ($TiO_2$) and silicon dioxide ($SiO_2$), and they may be used alone or in the form of a composite comprising an optional combination of two or more kinds thereof.

In this connection, it is preferred that the film has a thickness of 0.01 to 1.0 μm. If the thickness of the film is less than 0.01 μm, pin-holes will tend to often appear in the formed film, the effect of preventing water vapor or carbon dioxide gas from permeating the electrode will be lost, and simultaneously the mechanical strength of the film will be deteriorated and it will be liable to break. In contrast, if the thickness of the film is more than 1.0 μm, the amount of oxygen gas to be allowed to permeate therethrough will be reduced, which fact will deteriorate a heavy-load discharge function of the prepared electrode.

In the composite membrane according to this invention, any porous material may be employed for the porous membrane so long as it has fine pores as small as 0.1 μm or less in pore size. In view of the fact that the porous membrane will be deposited on the electrode body, it is preferably rich in flexibility. Further, the preferred porous membrane has its fine pores distributed in a uniform state, and it is also preferred that the proportion of the space volume of the fine pores to the total volume of the membrane is within the range of 0.1 to 90%.

Examples of such porous membrane include a porous fluororesin membrane (Fluoropore® (trade name) made by Sumitomo Electric Ind., Ltd.), a porous polycarbonate membrane (Nuclepore (trade name) made by Nuclepore Corp.), a porous cellulose ester membrane (Millipore Membrane Filter (trade name) made by Millipore Corp.) and a porous polypropylene membrane (Celgard (trade name) made by Celanese Plastics Company). When the pore size of the porous membrane exceeds a level of 0.1 μm, a pin-holes will very often occur in a film made of a metallic oxide or a water repellent layer, which will be described hereinafter, deposited on the porous membrane. As a result, the effect of preventing water vapor or carbon dioxide gas from permeating the electrode will be lost, and the layer will be reduced in mechanical strength and will be liable to break.

Next, a material constituting the water repellent layer should have water repellent properties and electrolyte-resistant properties, and examples of such practicable materials include polytetrafluoroethylene (PTFE), fluoroethylene-propylene (FEP), polyphenylene oxide (PPO), polyphenylene sulfide (PPS), polyethylene (PE), polypropylene (PP), copolymers thereof, and mixtures thereof.

In a material to be thermally fused and bonded such as fluoroethylene-propylene (FEP), polyethylene (PE) or ethylene-tetrafluoroethylene copolymer is used for the water repellent layer, the mechanical strength of the prepared composite membrane can be increased with the aid of a suitable thermal treatment.

Examples of materials for the water repellent layer used in this invention include, in addition to the above-mentioned ones, a variety of organic compounds which are formed on the porous membrane as a thin film by means of a plasma polymerization, for example, fluorinated organic compounds such as benzotrifluoride, m-chlorobenzotrifluoride, hexafluorobenzene, pentafluorobenzene, pentafluorostyrene, and mixtures thereof; and hydrocarbon series compounds such as $C_1$ to $C_{12}$ saturated hydrocarbon compounds, $C_1$ to $C_{12}$ unsaturated hydrocarbon compounds, $C_1$ to $C_{14}$ alkylbenzene compounds, styrene, α-methylstyrene and mixtures thereof. The layers all comprising these recited materials do not allow pin-holes to appear and are excellent in selective permeability to oxygen gas. Particularly, the aforementioned fluorinated organic compounds are more useful, because their water repellent layers prepared by the use of the plasma polymerization of their monomolecules are excellent in the effect of preventing water vapor or carbon dioxide gas from permeating the electrode. The thickness of the practicable water repellent layer is preferably within the range of 0.01 to 1.0 μm, and when the thickness is less than 0.01 μm, the water repellent layer will be formed in a mottling state and thus cannot cover uniformly the surface of the porous membrane, which fact will lead to the decrease in the effect of inhibiting the permeation of water vapor or carbon dioxide gas through the electrode, and accordingly the mechanical strength of the whole layer will deteriorate. Conversely, when the thickness of the water repellent layer is in excess of 1.0 μm, the amount of oxygen gas to be fed to the electrode will be insufficient with the result that the electric discharge properties of the prepared electrode will deteriorate (i.e., the heavy-load discharge will become difficult).

Further, the water repellent layer may be formed in the style of a single layer, but on this layer a thin layer comprising an organic compound other than the material of the former layer may be superincumbently formed.

On the thus formed water repellent layer, the film of the water-containable or wettable metallic oxide is to be further superimposed. The thickness of the oxide film is preferably within the range of 0.01 to 1.0 μm for the same reason as in the case of the water repellent layer. The oxygen gas permselective membrane according to this invention may be prepared as follows:

First, in the case of the oxygen gas permselective membrane comprising the thin layer made of the water-containable or wettable metallic oxide, the deposition of the film may be carried out preferably by a deposition process or sputtering process which is prevalent as a film-forming process. When the deposition process is employed, the film may be formed, for example, the material which is to be formed a film is set on the vacuum depositing equipment, the temperature therein is maintain at 150° C. and the partial pressure of oxygen in the equipment is adjusted to $5 \times 10^{-3}$ Torr using a metal as a deposition source which is formable an aforementioned metallic oxide. And in the case of the sputtering process, forming the film may be accomplished, for example, by use of the water-containable or wettable metallic oxide as a sputtering source in a mixed gas of argon and oxygen (Ar: 90 vol%, $O_2$: 10 vol%) having a pressure of $2 \times 10^{-3}$ Torr and at a high-frequency power of 100 W.

Second, in the case of the composite membrane having a two-layer structure, a film of the water-containable or wettable metallic oxide may be deposited directly on either surface of the aforementioned porous membrane in the same procedures as mentioned above.

Third, in the case of a composite membrane having a three-layer structure, the water repellent layer is formed on either surface of the porous membrane, and the film of the water-containable or wettable metallic oxide is then deposited on the just prepared water repellent layer by applying such a deposition process or sputtering process as in the case of the oxygen gas permselective membrane of the single layer structure described above.

In the respective cases of the above-mentioned three structures, the metallic oxide itself can be applied as a deposition source of sputtering in forming the film of the water-containable or wettable metallic oxide. However, it is preferred that a metallic simple substance for producing a metallic oxide by a reaction with oxygen is used as the deposition source or sputtering source and a used atmosphere contains oxygen, because under such conditions, the rate of forming the film of the metallic oxide will be accelerated and the operation of forming the film will become easy.

An air electrode in which the oxygen gas permselective membrane according to this invention is used may take, for example, the following constitution:

The air electrode including the oxygen gas permselective membrane according to this invention comprises a porous electrode body having an electrochemical reducing function to oxygen gas and simultaneously having a current collecting function, and the film of the water-containable or wettable metallic oxide which is, integrally and directly or via a porous membrane, deposited on the gas-side surface of the electrode body. Manufacturing the air electrode can be carried out by depositing the film of the water-containable or wettable metallic oxide on the gas-side surface of the porous electrode body having the electrochemical reducing function to oxygen gas and simultaneously having the current collecting function by means of a deposition process or sputtering process. Alternatively, the air electrode can be otherwise manufactured by depositing the film of the water-containable or wettable metallic oxide on one surface of the porous membrane of 0.1 $\mu$m or less in pore diameter by means of the deposition process or sputtering process, and by compressedly bonding integrally another surface of the porous membrane to the gas-side surface of the electrode body having the electrochemical reducing function to oxygen gas and simultaneously having the current collecting function.

The electrode body used in the air electrode with respect to this invention has an active function for reducing electrochemically oxygen gas (for ionizing oxygen gas), and the body is further conductive as well as porous. Materials for the electrode body include, for example, in addition to the aforesaid materials, a silver filter, Raney nickel, a sintered body of silver or nickel, a variety of foamed metals, a nickel-plated and pressed stainless steel thin wire, and a metallic porous material obtained by plating the thus treated stainless steel with gold, palladium or silver. For the purposes of removing promptly the reduced ionic products of oxygen gas, which have been produced by the electrode reaction in the pores of the electrode body, from these pores (reaction range), and of permitting a heavy-load discharge of, for example, 50 mA/cm$^2$ or more to smoothly continue, it is preferred that the pores distributed in the electrode body have a pore size of 0.1 to 10 $\mu$m or so.

The air electrode just described has the structure that the film made of the water-containable or wettable metallic oxide is integrally deposited, directly or via a porous membrane, on the gas-side surface of such an electrode body as mentioned above.

In order to deposit integrally the film of the water containable or wettable metallic oxide on the gas-side surface of the electrode body, the following procedures may be applied:

A first procedure comprises depositing directly the water-containable or wettable metallic oxide on the gas-side surface of the electrode body in an ordinary film-forming manner such as a vacuum deposition process or sputtering process in order to form the film having a desired thickness on the electrode body.

A second procedure comprises depositing directly the film of the water-containable or wettable metallic oxide on one surface of the porous membrane of 0.1 $\mu$m or less in pore size by means of the deposition process or sputtering process in order to prepare a composite membrane of a two-layer structure, and bonding compressedly and integrally another surface of the porous membrane, i.e. the surface, opposite to the surface having the film, of the composite membrane, to the gas-side surface of the electrode body under a predetermined pressure.

In the respective cases of the first and second procedures mentioned above, the water-containable or wettable metallic oxide itself can be applied as a deposition source or sputtering source in forming the film of the water-containable or wettable metallic oxide. However, it is preferred that a metallic simple substance for producing a metallic oxide by a reaction with oxygen is used as the deposition source or sputtering source and a used atmosphere contains oxygen, because under such conditions, the rate of forming the film of the metallic oxide will be accelerated and the operation of forming it will become easy.

Further, it is preferred that the film of the water-containable or wettable metallic oxide is adjusted to the range of 0.01 to 1.0 $\mu$m in thickness. If the thickness of the film is less than 0.01 $\mu$m, pin-holes will increase and the effect of preventing water vapor or carbon dioxide gas from permeating the electrode will be reduced, and the mechanical strength of the layer will be deteriorated, so that it will be liable to break. In contrast, if the thickness of the thin membrane is more than 1.0 $\mu$m, the amount of oxygen gas to be allowed to permeate therethrough will be reduced, which fact will render difficult the heavy-load discharge of the electrode.

Furthermore, for the porous membrane used in the second procedure described above, any material may be employed so long as the pore diameter is as small as 0.1 $\mu$m or less. Examples of such porous membranes include aforementioned porous membranes of a porous fluororesin membrane (Fluoropore (trade name) made by Sumitomo Electric Ind., Ltd.), a porous polycarbonate membrane (Nuclepore (trade name) made by Nuclepore Corp.), a porous cellulose ester membrane (Millipore Membrane Filter (trade name) made by Millipore Corp.) and a porous polypropylene membrane (Celgard (trade name) made by Celanese Plastics Company). When the film of water-containable or wettable metallic oxide is deposited on the porous membrane which embraces pores having a diameter more than 0.1 μm, pinholes will very often occur in the film, so that the function of the film will be lost and its mechanical strength will decrease, which fact will lead to the disadvantage that the film will be liable to break.

The thus prepared air electrode may be incorporated into a cell according to an ordinary manner. In this case, in order to permit the supply of momentary large current by the electrochemical reduction of an electrode-constituting element itself in addition to the electrochemical reduction of oxygen gas, it is preferable to deposit integrally, on the electrolyte side of the electrode body, a porous layer containing at least one of a metal, an oxide or a hydroxide in which oxidation state can vary by a more ignoble potential in the range of 0.4 V than the oxidation-reduction balanced potential of oxygen. This porous layer can be oxidized with oxygen gas by a local cell action during discharge at a light-load or at the time of open-circuit to return to the original oxidation state. Examples of materials constituting such porous layer include $Ag_2O$, $MnO_2$, $Co_2O_3$, $PbO_2$, a variety of perovskite type oxides and spinel type oxides.

The air electrode may be incorporated into a cell not only in a plate form but also in a cylindrical form. In the latter case, the plate air electrode may be bent to a cylinder-shape. For the purpose of imparting mechanical stability to the air electrode so that it may be guarded from breakage during the above bending operation, the film of the water-containable or wettable metallic oxide is preferably further deposited, on the gas-side surface thereof, integrally with a porous thin membrane such as a porous fluororesin membrane, a porous polycarbonate membrane, a porous cellulose ester membrane or a porous polypropylene membrane.

Now, this invention will be described in detail in accordance with the following Examples.

EXAMPLES 1 TO 9

Each porous polycarbonate membrane in which the fine pores having an average pore size of 0.03 μm are uniformly distributed and the pores of which have as much a space volume as 0.42% (Nuclepore (trade name) made of Nuclepore Corp. and having a thickness of 5 μm) was subjected to a sputtering treatment by use of Sn, Zn, Al, Mg, Ca, Sr, Ba, Ti or Si as a sputtering source in a mixed gas of argon and oxygen (consisting of 90% by volume of Ar and 10% by volume of $O_2$) having a pressure of $2 \times 10^{-3}$ Torr and at a high-frequency power of 100 W, in order to deposit each film of various water-containable or wettable metallic oxides on either side of the polycarbonate membrane, with the thickness of the obtained film being 0.2 μm.

EXAMPLES 10 TO 18

Sputtering of fluoroethylene propylene (FEP) was carried out for the same type of polycarbonate membranes as in Examples 1 to 9 in an argon gas having a pressure of $1 \times 10^{-2}$ Torr and at a high-frequency power of 200 W in order to deposit a water repellent layer of 0.2 μm in thickness on either surface of each membrane. The same procedure as in Examples 1 to 9 was then repeated to further deposit each film having a thickness of 0.2 μm of various water-containable or wettable metallic oxides on the water repellent layer already prepared on the polycarbonate membrane.

EXAMPLES 19 TO 27

The same type of polycarbonate membranes as in Examples 1 to 9 was placed in a plasma reaction tank, a high-frequency power of 13.56 MHz was applied to the tank from outside, an argon gas and a monomer gas of pentafluorostyrene were introduced into the tank at a flow rate of 600 ml/min, and a plasma polymerization reaction was then carried out therein under the condition of a radio-frequency output of 0.4 W/cm² in order to deposit a 0.2 μm-thick layer of the pentafluorostyrene polymer on either surface of each polycarbonate membrane.

Further, each film (0.2 μm) of various water-containable or wettable metallic oxides was then deposited on the already prepared layer in the same manner as in Examples 1 to 9.

The thus obtained 27 kinds of composite membrane were measured for oxygen-permeation rates ($J_{O_2}$: cc/sec.cm².cmHg) and carbon dioxide gas-permeation rates ($J_{CO_2}$: cc/sec.cm².cmHg) in accordance with an equable pressure method in which a gas chromatograph is employed as a detecting means, and for water vapor-permeation rates ($J_{H_2O}$: cc/sec.cm².cmHg) in a manner corresponding to JIS Z 0208 (a cup method). Afterward, ratios ($J_{O_2}/J_{H_2O}$ and $J_{O_2}/J_{CO_2}$) of $J_{H_2O}$ and $J_{CO_2}$ to $J_{O_2}$ were calculated out, which ratios can be taken as gas permeation ratios.

For comparison, the measurements of $J_{O_2}$, $J_{H_2O}$ and $J_{CO_2}$ were similarly carried out for a polysiloxane membrane (Comparative Example 1) of 50 μm in thickness, an intermediate density polyethylene membrane of 20 μm in thickness (Comparative Example 2), a biaxially orientated polypropylene membrane (Comparative Example 3) of 20 μm in thickness, a polytetrafluoroethylene membrane (Comparative Example 4) of 20 μm in thickness, a commercially available FEP membrane (Comparative Example 5) of 20 μm in thickness, and an FEP membrane (Comparative Example 6) of 0.2 μm in thickness which was deposited by the same sputtering process as in Example 10 to 18. And the ratios of $J_{O_2}/J_{H_2O}$ and $J_{O_2}/J_{CO_2}$ were likewise calculated out.

Obtained results are set forth all together in Table 1 below:

TABLE 1

| | Membrane | | | | | | | |
| | Water repellent layer | Film of metallic oxide | Total thickness of composite membrane (μm) | $J_{O_2}$ (cc/sec · cm² · cmHg) | $J_{H_2O}$ (cc/sec · cm² · cmHg) | $J_{CO_2}$ (cc/sec · cm² · cmHg) | $J_{O_2}/J_{H_2O}$ | $J_{O_2}/J_{CO_2}$ |
| --- | --- | --- | --- | --- | --- | --- | --- | --- |
| Example 1 | — | $SnO_2$ | 5.2 | $1.7 \times 10^{-5}$ | $8.5 \times 10^{-6}$ | $1.1 \times 10^{-5}$ | 2.0 | 1.5 |

TABLE 1-continued

| | Membrane | | | | | | | |
|---|---|---|---|---|---|---|---|---|
| | Water repellent layer | Film of metallic oxide | Total thickness of composite membrane ($\mu$m) | $J_{O_2}$ (cc/sec · cm² · cmHg) | $J_{H_2O}$ (cc/sec · cm² · cmHg) | $J_{CO_2}$ (cc/sec · cm² · cmHg) | $J_{O_2}/J_{H_2O}$ | $J_{O_2}/J_{CO_2}$ |
| Example 2 | — | ZnO | " | $2.0 \times 10^{-5}$ | $1.2 \times 10^{-5}$ | $1.5 \times 10^{-5}$ | 1.7 | 1.3 |
| Example 3 | — | Al$_2$O$_3$ | " | $1.9 \times 10^{-5}$ | $1.0 \times 10^{-5}$ | $1.4 \times 10^{-5}$ | 1.9 | 1.4 |
| Example 4 | — | MgO | " | $2.1 \times 10^{-5}$ | $1.3 \times 10^{-5}$ | $1.8 \times 10^{-5}$ | 1.6 | 1.2 |
| Example 5 | — | CaO | " | $2.0 \times 10^{-5}$ | $1.2 \times 10^{-5}$ | $1.5 \times 10^{-5}$ | 1.7 | 1.3 |
| Example 6 | — | SrO | " | $2.2 \times 10^{-5}$ | $1.4 \times 10^{-5}$ | $1.8 \times 10^{-5}$ | 1.6 | 1.2 |
| Example 7 | — | BaO | " | $2.1 \times 10^{-5}$ | $1.3 \times 10^{-5}$ | $1.8 \times 10^{-5}$ | 1.6 | 1.2 |
| Example 8 | — | TiO$_2$ | " | $2.3 \times 10^{-5}$ | $1.3 \times 10^{-5}$ | $1.6 \times 10^{-5}$ | 1.8 | 1.4 |
| Example 9 | — | SiO$_2$ | " | $2.1 \times 10^{-5}$ | $1.1 \times 10^{-5}$ | $1.5 \times 10^{-5}$ | 1.9 | 1.4 |
| Example 10 | FEP | SnO$_2$ | 5.4 | $2.1 \times 10^{-5}$ | $2.8 \times 10^{-6}$ | $8.4 \times 10^{-6}$ | 7.5 | 2.5 |
| Example 11 | " | ZnO | " | $2.6 \times 10^{-5}$ | $3.6 \times 10^{-6}$ | $1.1 \times 10^{-5}$ | 7.2 | 2.4 |
| Example 12 | " | Al$_2$O$_3$ | " | $2.4 \times 10^{-5}$ | $3.2 \times 10^{-6}$ | $9.6 \times 10^{-6}$ | 7.5 | 2.5 |
| Example 13 | " | MgO | " | $2.9 \times 10^{-5}$ | $4.1 \times 10^{-6}$ | $1.3 \times 10^{-5}$ | 7.1 | 2.2 |
| Example 14 | " | CaO | " | $2.9 \times 10^{-5}$ | $4.0 \times 10^{-6}$ | $1.3 \times 10^{-5}$ | 7.2 | 2.2 |
| Example 15 | " | SrO | " | $3.0 \times 10^{-5}$ | $4.2 \times 10^{-6}$ | $1.4 \times 10^{-5}$ | 7.1 | 2.1 |
| Example 16 | " | BaO | " | $2.9 \times 10^{-5}$ | $4.1 \times 10^{-6}$ | $1.3 \times 10^{-5}$ | 7.1 | 2.2 |
| Example 17 | " | TiO$_2$ | " | $2.3 \times 10^{-5}$ | $3.1 \times 10^{-6}$ | $9.2 \times 10^{-6}$ | 7.4 | 2.5 |
| Example 18 | " | SiO$_2$ | " | $2.4 \times 10^{-5}$ | $3.2 \times 10^{-6}$ | $9.6 \times 10^{-6}$ | 7.5 | 2.5 |
| Example 19 | Pentafluorostyrene polymer membrane | SnO$_2$ | " | $2.1 \times 10^{-5}$ | $2.8 \times 10^{-6}$ | $8.4 \times 10^{-6}$ | 7.5 | 2.5 |
| Example 20 | Pentafluorostyrene polymer membrane | ZnO | " | $2.6 \times 10^{-5}$ | $3.6 \times 10^{-6}$ | $1.1 \times 10^{-5}$ | 7.2 | 2.4 |
| Example 21 | Pentafluorostyrene polymer membrane | Al$_2$O$_3$ | " | $2.4 \times 10^{-5}$ | $3.2 \times 10^{-6}$ | $9.6 \times 10^{-6}$ | 7.5 | 2.5 |
| Example 22 | Pentafluorostyrene polymer membrane | MgO | " | $2.9 \times 10^{-5}$ | $4.1 \times 10^{-6}$ | $1.3 \times 10^{-5}$ | 7.1 | 2.2 |
| Example 23 | Pentafluorostyrene polymer membrane | CaO | " | $2.9 \times 10^{-5}$ | $4.0 \times 10^{-6}$ | $1.3 \times 10^{-5}$ | 7.2 | 2.2 |
| Example 24 | Pentafluorostyrene polymer membrane | SrO | " | $3.0 \times 10^{-5}$ | $4.2 \times 10^{-6}$ | $1.4 \times 10^{-5}$ | 7.1 | 2.1 |
| Example 25 | Pentafluorostyrene polymer membrane | BaO | " | $2.9 \times 10^{-5}$ | $4.1 \times 10^{-6}$ | $1.3 \times 10^{-5}$ | 7.1 | 2.2 |
| Example 26 | Pentafluorostyrene polymer membrane | TiO$_2$ | " | $2.3 \times 10^{-5}$ | $3.1 \times 10^{-6}$ | $9.2 \times 10^{-6}$ | 7.4 | 2.5 |

TABLE 1-continued

| | Membrane | | | | | | |
|---|---|---|---|---|---|---|---|
| | Water repellent layer | Film of metallic oxide | Total thickness of composite membrane ($\mu$m) | $J_{O_2}$ (cc/sec · cm² · cmHg) | $J_{H_2O}$ (cc/sec · cm² · cmHg) | $J_{CO_2}$ (cc/sec · cm² · cmHg) | $J_{O_2}/J_{H_2O}$ | $J_{O_2}/J_{CO_2}$ |
| Example 27 | Pentafluorostyrene polymer membrane | SiO$_2$ | " | $2.4 \times 10^{-5}$ | $3.2 \times 10^{-6}$ | $9.6 \times 10^{-6}$ | 7.5 | 2.5 |
| Comparative Example 1 | Polysiloxane membrane | | 50 | $1.2 \times 10^{-5}$ | $3.7 \times 10^{-4}$ | $7.5 \times 10^{-5}$ | $3.2 \times 10^{-2}$ | 0.16 |
| Comparative Example 2 | Polyethylene membrane | | 20 | $1.6 \times 10^{-7}$ | $4.7 \times 10^{-6}$ | $7.6 \times 10^{-7}$ | $3.4 \times 10^{-2}$ | 0.21 |
| Comparative Example 3 | Polypropylene membrane | | 20 | $3.6 \times 10^{-8}$ | $2.4 \times 10^{-6}$ | $1.12 \times 10^{-7}$ | $1.5 \times 10^{-2}$ | 0.32 |
| Comparative Example 4 | Polytetrafluoroethylene membrane | | 20 | $2.1 \times 10^{-7}$ | $4.1 \times 10^{-6}$ | $5.8 \times 10^{-7}$ | $5.1 \times 10^{-2}$ | 0.36 |
| Comparative Example 5 | Commercially available FEP membrane | | 20 | $2.5 \times 10^{-7}$ | $2.7 \times 10^{-6}$ | $6.6 \times 10^{-7}$ | $9.2 \times 10^{-2}$ | 0.38 |
| Comparative Example 6 | FEP sputtered membrane | | 0.2 | $7.2 \times 10^{-5}$ | $6.5 \times 10^{-4}$ | $7.3 \times 10^{-5}$ | 0.11 | 0.99 |

EXAMPLES 28 TO 36

There were used, as electrode bodies, Raney nickel plates (200 $\mu$m in thickness) where the average pore size of each plate was 5 $\mu$m and its porosity was 80%. Each plate was set on a vacuum depositing equipment, the temperature therein was maintained at 150° C., and the partial pressure of oxygen in the equipment was then adjusted to $5 \times 10^{-3}$ Torr. As deposition sources, 9 metals of Sn, Zn, Al, Mg, Ca, Sr, Ba, Ti and Si were each selected.

An ordinary deposition process has been employed to directly deposit each aforementioned metal on either surface of the Raney nickel plate. In every case, a metallic oxide of 0.2 $\mu$m in thickness was deposited on the surface of the Raney nickel.

The thus obtained metallic oxide-deposited Raney nickels were dipped into a 2% palladium chloride solution and were subjected to cathodic polarization in order to deposit thereon a palladium layer having a thickness of about 0.5 $\mu$m inclusive of palladium in pores on the Raney nickel plate. The thus obtained products are air electrodes.

EXAMPLES 37 TO 45

The same manner as in Examples 28 to 36 was repeated except that the deposition process was replaced with a sputtering process. The sputtering treatment was carried out in a mixed gas of argon and oxygen (consisting of 90% by volume of Ar and 10% by volume of O$_2$) at a pressure of $2 \times 10^{-3}$ Torr and under a high-frequency power of 100 W. Every film of the metallic oxide had a thickness of 0.2 $\mu$m.

EXAMPLES 46 TO 54

Porous polycarbonate membranes (Nuclepore (trade name) made by Nuclepore Corp.) in which pores of 0.03 $\mu$m in average diameter were uniformly distributed were each set on a vacuum depositing equipment and an ambient temperature was maintained at 100° C. The partial pressure of oxygen in the equipment was adjusted to a level of $5 \times 10^{-3}$ Torr, and the same deposition sources as used in Examples 28 to 36 were applied in order to deposit each 0.2-$\mu$m-thick film of the metallic oxides on either surface of the membrane. Afterward, each porous membrane was compressedly bonded, on another surface thereof, to either surface of the Raney nickel plate (200 $\mu$m in thickness) having an average pore size of 5 $\mu$m and a porosity of 80%.

The thus treated Raney nickel plates were each dipped into a 2% palladium chloride solution and were each subjected to cathodic polarization in order to deposit thereon a palladium layer having a thickness of about 0.5 $\mu$m inclusive of palladium in pores on the Raney nickel plate. The thus obtained products are air electrodes.

EXAMPLES 55 TO 63

The same manner as in Examples 46 to 54 was repeated except that the deposition process was replaced with the sputtering process under the same sputtering conditions as used in Examples 37 to 45 in order to prepare air electrodes.

COMPARATIVE EXAMPLE 7

After active carbon powder was suspended in an aqueous palladium chloride solution, reduction treatment was carried out by the use of formalin in order to obtain the active carbon powder wearing palladium. Then, the obtained powder was subjected to a waterproof treatment with a 10 to 15% polytetrafluoroethylene dispersion, was mixed with a PTFE powder as a binding agent, and was then rolled to a sheet. The thus prepared sheet was compressedly bonded to a nickel net in order to obtain an electrode body of 0.6 mm in thickness. On the other hand, an artificial graphite powder was mixed with a PTFE dispersion, followed by a heat treatment to prepare a waterproof graphite powder. A PTFE powder which was a binding agent was mixed with this graphite powder, and the resultant mixture was then rolled to a sheet. The thus obtained sheet was compressedly bonded to the already obtained electrode body in order to prepare an air electrode of 1.6 mm in thickness.

COMPARATIVE EXAMPLE 8

A polysiloxane membrane (50 μm in thickness) which was a membrane for allowing oxygen gas to selectively permeate therethrough was compressedly bonded to either surface of a Raney nickel plate (200 μm in thickness) having an average pore diameter of 5 μm and a porosity of 80%, and the whole membrane was subjected to cathodic polarization in a 2% palladium chloride solution in order to deposit thereon a palladium layer having a thickness of 0.5 μm inclusive of palladium in pores on the Raney nickel plate. The thus obtained product is the air electrode.

COMPARATIVE EXAMPLE 9

A water vapor-absorbing layer comprising calcium chloride was deposited on the air-side surface of the air electrode prepared in Comparative Example 7.

COMPARATIVE EXAMPLE 10

A thin layer of $SnO_2$ having a thickness of 0.2 μm was deposited on one surface of a 5-μm-thick porous polycarbonate membrane (Nuclepore (trade name) made by Nuclepore Corp.) in which pores of 0.15 μm in average pore size were distributed, and another surface of the membrane above was compressedly bonded to either surface of a Raney nickel plate having an average pore diameter of 5 μm and a porosity of 80%. The whole plate was dipped into a 2% palladium chloride solution and was subjected to cathodic polarization in order to deposit thereon a palladium layer of about 0.5 μm in thickness inclusive of palladium in pores on the Raney nickel plate. The thus obtained product is an air electrode.

COMPARATIVE EXAMPLE 11

The same manner as in Comparative Example 10 was repeated with the exception that there was employed a porous polycarbonate membrane having an average pore size of 0.03 μm and was deposited a film of $SnO_2$ having a thickness of 0.005 μm in order to prepare a desired air electrode.

COMPARATIVE EXAMPLE 12

The procedure described in Example 11 was repeated except that a film of $SnO_2$ having a thickness of 2.0 μm was deposited in order to prepare an air electrode.

Next, an air-zinc cell was assembled by the use of each of 42 air electrodes thus prepared above, an opposite electrode of a geled zinc which was amalgamated with 3% by weight of mercury, an electrolyte of potassium hydroxide, and a separator of a polyamide nonwoven fabric material.

These assembled 42 cells were then allowed to stand in air at 25° C. for 16 hours. Afterward, measurement was carried out for the current density of each cell at the time when a terminal voltage dropped below 1.0 V after 5 minutes' discharge under a variety of currents. Further, each cell was stored in an atmosphere at 45° C. and at a relative humidity of 90%, and the leakage state of a used electrolyte was observed.

Moreover, the same discharge test as mentioned above was carried out for each cell which had undergone the above storage step, and the proportion (%) of a current value at this test time to an initial current value was calculated out. The thus calculated values each represent a degradation level of the air electrode in the cell and can be taken as a maintenance proportion of its discharge properties. In other words, it can be meant that the greater this value, the smaller the deterioration in the air electrode is.

Further, the film deposited on each electrode was measured for a permeability rate to oxygen gas in accordance with an equable pressure method in which a gas chromatograph is employed as a detecting means, and for a permeability rate to water-vapor in a manner corresponding to JIS Z 0208 (a cup method). Afterward, ratios of both the rates were calculated out.

The obtained results are set forth in Table 2 below:

TABLE 2

| | Electrode body | | Water-containable or wettable metallic oxide | | Porous membrane (pore size: μm) | Deposition manner of film | Current density (mA/cm²) | Maintenance proportion of discharge properties (%) | Gas permeation ratio of film ($O_2/H_2O$) |
|---|---|---|---|---|---|---|---|---|---|
| | Type | Thickness (μm) | Type | Thickness (μm) | | | | | |
| Example 28 | Raney nickel | 200 | $SnO_2$ | 0.2 | Absent | Deposition process | 59 | 75 | 1.9 |
| Example 29 | " | " | ZnO | " | " | " | 57 | 74 | 1.6 |
| Example 30 | " | " | $Al_2O_3$ | " | " | " | 58 | 73 | 1.8 |
| Example 31 | " | " | MgO | " | " | " | 56 | 74 | 1.5 |
| Example 32 | " | " | CaO | " | " | " | 56 | 74 | 1.6 |
| Example 33 | " | " | SrO | " | " | " | 55 | 73 | 1.5 |
| Example 34 | " | " | BaO | " | " | " | 55 | 73 | 1.5 |
| Example 35 | " | " | $TiO_2$ | " | " | " | 58 | 73 | 1.7 |
| Example 36 | " | " | $SiO_2$ | " | " | " | 57 | 74 | 1.8 |
| Example 37 | " | " | $SnO_2$ | " | " | Sputtering process | 59 | 75 | 2.0 |
| Example 38 | " | " | ZnO | " | " | " | 57 | 74 | 1.7 |
| Example 39 | " | " | $Al_2O_3$ | " | " | " | 58 | 73 | 1.9 |
| Example 40 | " | " | MgO | " | " | " | 56 | 74 | 1.6 |
| Example 41 | " | " | CaO | " | " | " | 56 | 74 | 1.7 |
| Example 42 | " | " | SrO | " | " | " | 55 | 73 | 1.6 |
| Example 43 | " | " | BaO | " | " | " | 55 | 73 | 1.6 |

TABLE 2-continued

| | Electrode body | | Water-containable or wettable metallic oxide | | Porous membrane (pore size: μm) | Deposition manner of film | Current density (mA/cm²) | Maintenance proportion of discharge properties (%) | Gas permeation ratio of film (O₂/H₂O) |
|---|---|---|---|---|---|---|---|---|---|
| | Type | Thickness (μm) | Type | Thickness (μm) | | | | | |
| Example 44 | " | " | TiO₂ | " | " | " | 58 | 73 | 1.8 |
| Example 45 | " | " | SiO₂ | " | " | " | 57 | 74 | 1.9 |
| Example 46 | " | " | SnO₂ | " | present: 0.03 μm | Compressive bonding after deposition | 59 | 76 | 1.9 |
| Example 47 | " | " | ZnO | " | present: 0.03 μm | Compressive bonding after deposition | 57 | 75 | 1.6 |
| Example 48 | " | " | Al₂O₃ | " | present: 0.03 μm | Compressive bonding after deposition | 58 | 74 | 1.8 |
| Example 49 | " | " | MgO | " | present: 0.03 μm | Compressive bonding after deposition | 56 | 75 | 1.5 |
| Example 50 | " | " | CaO | " | present: 0.03 μm | Compressive bonding after deposition | 56 | 75 | 1.6 |
| Example 51 | " | " | SrO | " | present: 0.03 μm | Compressive bonding after deposition | 55 | 74 | 1.5 |
| Example 52 | " | " | BaO | " | present: 0.03 μm | Compressive bonding after deposition | 55 | 74 | 1.5 |
| Example 53 | " | " | TiO₂ | " | present: 0.03 μm | Compressive bonding after deposition | 58 | 74 | 1.7 |
| Example 54 | " | " | SiO₂ | " | present: 0.03 μm | Compressive bonding after deposition | 57 | 75 | 1.8 |
| Example 55 | " | " | SnO₂ | " | present: 0.03 μm | Compressive bonding after sputtering | 59 | 77 | 2.0 |
| Example 56 | " | " | ZnO | " | present: 0.03 μm | Compressive bonding after sputtering | 57 | 76 | 1.7 |
| Example 57 | " | " | Al₂O₃ | " | present: 0.03 μm | Compressive bonding after sputtering | 58 | 75 | 1.9 |
| Example 58 | " | " | MgO | " | present: 0.03 μm | Compressive bonding after sputtering | 56 | 76 | 1.6 |
| Example 59 | " | " | CaO | " | present: 0.03 μm | Compressive bonding after sputtering | 56 | 76 | 1.7 |
| Example 60 | " | 41 | SrO | " | present: 0.03 μm | Compressive bonding after sputtering | 55 | 75 | 1.6 |
| Example 61 | " | " | BaO | " | present: 0.03 μm | Compressive bonding after sputtering | 55 | 75 | 1.6 |
| Example 62 | " | " | TiO₂ | " | present: 0.03 μm | Compressive bonding after sputtering | 58 | 75 | 1.8 |
| Example 63 | " | " | SiO₂ | " | present: 0.03 μm | Compressive bonding after sputtering | 57 | 76 | 1.9 |
| Comparative Example 7 | Active carbon with Palladium | 600 | — | — | Graphite + PTFE | Compressive bonding | 25 | 40 | — |
| Comparative Example 8 | Raney nickel | 200 | Polysiloxane membrane | | | Compressive bonding | 50 | 60 | 0.032 |
| Comparative Example 9 | Active carbon with Palladium | 600 | Graphite powder + PTFE | | | Compressive bonding | 20 | 50 | — |
| Comparative Example 10 | Raney nickel | 200 | SnO₂ | 0.2 | present: 0.15 μm | Compressive bonding after deposition | 59 | 42 | — |
| Comparative Example 11 | " | " | " | 0.005 | present: 0.03 μm | Compressive bonding after deposition | 58 | 41 | — |
| Comparative Example 12 | " | " | " | 2.0 | present: 0.03 μm | Compressive bonding after deposition | 12 | 90 | — |

EXAMPLES 64 TO 72

There were used, as electrode bodies, Raney nickel plates (200 μm in thickness) where the average pore size of each plate was 5 μm and its porosity was 80%. Sputtering of fluoroethylene propylene (FEP) was carried out for the one side of the Raney nickel plate in an argon gas having a pressure of $1 \times 10^{-2}$ Torr and at a high-frequency power of 200 W in order to deposit a water repellent layer of 0.2 μm in thickness on either surface of each membrane.

After each plate was set on a vacuum depositing equipment, the temperature of the side of FEP water repellent layer was maintained at 100° C., and the partial pressure of oxygen in the equipment was adjusted to $5 \times 10^{-3}$ Torr. As deposition sources, 9 metals of Sn, Zn, Al, Mg, Ca, Sr, Ba, Ti and Si were each selected. An ordinary deposition process has been employed to directly deposit each aforementioned metal on either surface of the FEP water repellent layer. In every case, a metallic oxide of 0.2 μm in thickness was deposited on the surface of the FEP water repellent layer.

The thus obtained metallic oxide-deposited plates were dipped into a 2% palladium chloride solution and were subjected to cathodic polarization in order to deposit thereon a palladium layer having a thickness of about 0.5 μm inclusive of palladium in pores on the Raney nickel plate. The thus obtained products are air electrode.

EXAMPLES 73 TO 81

The same manner as in Examples 64 to 72 was repeated except that the deposition process was replaced with a sputtering process when the water-containable or wettable metallic thin layer was formed on the surface of the FEP water repellent layer. The sputtering treatment was carried out in a mixed gas of argon and oxygen (consisting of 90% by volume of Ar and 10% by volume of $O_2$) at a pressure of $2 \times 10^{-3}$ Torr and under a high-frequency power of 100 W. Every film of the metallic oxide had a thickness of 0.1 μm.

EXAMPLES 82 TO 90

To one side of porous polycarbonate membrane (Nuclepore (trade name) made by Nuclepore Corp.) in which pores of 0.03 μm in average diameter were uniformly distributed, sputtering of fluoroethylene propylene (FEP) was carried out in an argon gas having a pressure of $1 \times 10^{-2}$ Torr and at a high-frequency power of 200 W in order to deposit a water repellent layer of 0.2 μm in thickness on either surface of each membrane.

After each plate was set on a vacuum depositing equipment, the temperature of the water repellent layer was maintained at 100° C. And the partial pressure of oxygen in the equipment was adjusted to $5 \times 10^{-3}$ Torr in order to form a thin layer of water-containable or wettable metallic oxide on the surface of the water repellent layer using the same deposition source as in Examples 64 to 72. In every case, a thin layer of 0.1 μm in thickness was deposited on the surface of the FEP water repellent layer.

The thus obtained porous polycarbonate membrane of the composite thin membrane was compressedly bonded to either surface of the Raney nickel plate (200 μm in thickness) having an average pore size of 5 μm and a porosity of 80%.

The thus obtained metallic oxide-deposited plates were dipped into a 2% palladium chloride solution and were subjected to cathodic polarization in order to deposit thereon a palladium layer having a thickness of about 0.5 μm inclusive of palladium in pores on the Raney nickel plate. The thus obtained products are air electrodes.

EXAMPLES 91 TO 99

The same manner as in Examples 82 to 90 was repeated except that the deposition process was replaced with a sputtering process when the water-containable or wettable metallic thin layer was formed on the surface of the FEP water repellent layer. In this case, the sputtering treatment was carried out in a mixed gas of argon and oxygen (consisting of 90% by volume of Ar and 10% by volume of $O_2$) at a pressure of $2 \times 10^{-3}$ Torr and under a high-frequency power of 100 W. Every thin layer of the metallic oxide had a thickness of 0.1 μm.

These assembled 36 cells were then allowed to stand in air at 25° C. for 16 hours. Afterward, measurement was carried out for the current density, the maintenance proportion of their discharge properties and the gas permeation ratio of the film of each cell as the same procedures in Examples 28 to 63.

The obtained results are set forth in Table 3 below:

TABLE 3

|  | Electrode body | | Water repellent layer | | Water-containable or wettable metallic oxide thin layer | | Porous membrane (Present: Pore Size) | Deposition manner of film | Current density (mA/cm$^2$) | Maintenance proportion of discharge properties (%) | Gas permeation ratio of film ($O_2/H_2O$) |
|---|---|---|---|---|---|---|---|---|---|---|---|
|  | Type | Thickness (μm) | Type | Thickness (μm) | Type | Thickness (μm) |  |  |  |  |  |
| Example 64 | Raney nickel | 200 | FEP | 0.2 | SnO$_2$ | 0.2 | Absent | Sputtering → Deposition | 60 | 92 | 7.4 |
| Example 65 | Raney nickel | " | " | " | ZnO | " | " |  | 58 | 91 | 7.1 |
| Example 66 | Raney nickel | " | " | " | Al$_2$O$_3$ | " | " | Sputtering → Deposition | 59 | 90 | 7.4 |
| Example 67 | Raney nickel | " | " | " | MgO | " | " | Sputtering → Deposition | 57 | 92 | 7.0 |
| Example 68 | Raney nickel | " | " | " | CaO | " | " | Sputtering → Deposition | 57 | 92 | 7.1 |
| Example 69 | Raney nickel | " | " | " | SrO | " | " | Sputtering → Deposition | 56 | 91 | 7.0 |
| Example 70 | Raney nickel | " | " | " | BaO | " | " | Sputtering → Deposition | 56 | 91 | 7.0 |
| Example 71 | Raney nickel | " | " | " | TiO$_2$ | " | " | Sputtering → Deposition | 59 | 90 | 7.3 |

TABLE 3-continued

| | Electrode body | | Water repellent layer | | Water-containable or wettable metallic oxide thin layer | | Porous membrane (Present: Pore Size) | Deposition manner of film | Current density (mA/cm²) | Maintenance proportion of discharge properties (%) | Gas permeation ratio of film (O₂/H₂O) |
|---|---|---|---|---|---|---|---|---|---|---|---|
| | Type | Thickness (μm) | Type | Thickness (μm) | Type | Thickness (μm) | | | | | |
| Example 72 | Raney nickel | " | " | " | SiO₂ | " | " | Sputtering → Deposition | 58 | 91 | 7.4 |
| Example 73 | Raney nickel | " | " | " | SnO₂ | 0.1 | " | Sputtering → Sputtering | 60 | 92 | 7.5 |
| Example 74 | Raney nickel | " | " | " | ZnO | " | " | Sputtering → Sputtering | 58 | 91 | 7.2 |
| Example 75 | Raney nickel | " | " | " | Al₂O₃ | " | " | Sputtering → Sputtering | 59 | 90 | 7.5 |
| Example 76 | Raney nickel | " | " | " | MgO | " | " | Sputtering → Sputtering | 57 | 92 | 7.1 |
| Example 77 | Raney nickel | " | " | " | CaO | " | " | Sputtering → Sputtering | 57 | 92 | 7.2 |
| Example 78 | Raney nickel | " | " | " | SrO | " | " | Sputtering → Sputtering | 56 | 91 | 7.1 |
| Example 79 | Raney nickel | " | " | " | BaO | " | " | Sputtering → Sputtering | 56 | 91 | 7.1 |
| Example 80 | Raney nickel | " | " | " | TiO₂ | " | " | Sputtering → Sputtering | 59 | 90 | 7.4 |
| Example 81 | Raney nickel | " | " | " | SiO₂ | " | " | Sputtering → Sputtering | 58 | 91 | 7.5 |
| Example 82 | Raney nickel | " | " | " | SnO₂ | " | present: 0.03 μm | Sputtering → Deposition → Compressive bonding | 60 | 93 | 7.4 |
| Example 83 | Raney nickel | " | " | " | ZnO | " | present: 0.03 μm | Sputtering → Deposition → Compressive bonding | 58 | 92 | 7.1 |
| Example 84 | Raney nickel | " | " | " | Al₂O₃ | " | present: 0.03 μm | Sputtering → Deposition → Compressive bonding | 59 | 91 | 7.4 |
| Example 85 | Raney nickel | " | " | " | MgO | " | present: 0.03 μm | Sputtering → Deposition → Compressive bonding | 57 | 93 | 7.0 |
| Example 86 | Raney nickel | " | " | " | CaO | " | present: 0.03 μm | Sputtering → Deposition → Compressive bonding | 57 | 93 | 7.1 |
| Example 87 | Raney nickel | " | " | " | SrO | " | present: 0.03 μm | Sputtering → Deposition → Compressive bonding | 56 | 92 | 7.0 |
| Example 88 | Raney nickel | " | " | " | BaO | " | present: 0.03 μm | Sputtering → Deposition → Deposition bonding | 56 | 92 | 7.0 |
| Example 89 | Raney nickel | " | " | " | TiO₂ | " | present: 0.03 μm | Sputtering → Deposition → Compressive bonding | 59 | 91 | 7.3 |
| Example 90 | Raney nickel | " | " | " | SiO₂ | " | present: 0.03 μm | Sputtering → Deposition → Compressive bonding | 58 | 92 | 7.4 |
| Example 91 | Raney nickel | " | " | " | SnO₂ | " | present: 0.03 μm | Sputtering → Sputtering → Compressive bonding | 60 | 94 | 7.5 |
| Example 92 | Raney nickel | " | " | " | ZnO | " | present: 0.03 μm | Sputtering → Sputtering → Compressive bonding | 58 | 93 | 7.2 |
| Example 93 | Raney nickel | " | " | " | Al₂O₃ | " | present: 0.03 μm | Sputtering → Sputtering → Compressive bonding | 59 | 92 | 7.5 |
| Example 94 | Raney nickel | " | " | " | MgO | " | present: 0.03 μm | Sputtering → Sputtering → Compressive bonding | 57 | 94 | 7.1 |
| Example 95 | Raney nickel | " | " | " | CaO | " | present: 0.03 μm | Sputtering → Sputtering | 57 | 94 | 7.2 |

TABLE 3-continued

| | Electrode body | | Water repellent layer | | Water-containable or wettable metallic oxide thin layer | | Porous membrane (Present: Pore Size) | Deposition manner of film | Current density (mA/cm$^2$) | Maintenance proportion of discharge properties (%) | Gas permeation ratio of film (O$_2$/H$_2$O) |
|---|---|---|---|---|---|---|---|---|---|---|---|
| | Type | Thickness ($\mu$m) | Type | Thickness ($\mu$m) | Type | Thickness ($\mu$m) | | | | | |
| Example 96 | Raney nickel | " | " | " | SrO | " | present: 0.03 $\mu$m | Sputtering → Sputtering → Compressive bonding | 56 | 93 | 7.1 |
| Example 97 | Raney nickel | " | " | " | BaO | " | present: 0.03 $\mu$m | Sputtering → Sputtering → Compressive bonding | 56 | 93 | 7.1 |
| Example 98 | Raney nickel | " | " | " | TiO$_2$ | " | present: 0.03 $\mu$m | Sputtering → Sputtering → Compressive bonding | 59 | 92 | 7.4 |
| Example 99 | Raney nickel | " | " | " | SiO$_2$ | " | present: 0.03 $\mu$m | Sputtering → Sputtering → Compressive bonding | 58 | 93 | 7.5 |

The performance assessment of the air electrodes in Examples above was determined using potassium hydroxide as an electrolyte. However, it is definite that similar effects can also be obtained, needless to say, by use of another electrolyte, for example, ammonium chloride, sodium hydroxide, or an electrolyte which is added rubidium hydroxide, lithium hydroxide, cesium hydroxide or the like to the aforementioned electrolyte. Additionally, it has been found that the air-electrode in which the composite membrane with respect to this invention is employed can be applied in an air-iron cell.

As is apparent from the above description, the oxygen gas permselective membrane according to this invention, though being very thin, does not allow water vapor and carbon dioxide gas in air to permeate therethrough and has a great function for allowing oxygen gas to selectively permeate therethrough. Therefore, the air electrode comprising a combination of this oxygen gas permselective membrane and the electrode body may be designed overall in a thin form and enables a heavy-load discharge for a long period of time. It is noteworthy that such an air electrode also improves in storage properties and leakage resistance.

Therefore, it can be estimated that the oxygen gas permselective membrane according to this invention is industrially highly valuable and beneficial.

Further, the air electrode in which the aforementioned oxygen gas permselective membrane is employed may be designed overall in a thin structure and does not allow water vapor or carbon dioxide gas in air to permeate the electrode body. Therefore, such an electrode can be utilized for a prolonged heavy-load discharge and is excellent in storage properties. It can thus be concluded that such an air electrode is industrially valuable and beneficial.

We claim:

1. An oxygen gas permselective membrance which comprises a film consisting essentially of a water-containable or wettable metallic oxide which comprises at least one selected from the group consisting of stannic oxide, zinc oxide, aluminum oxide, magnesium oxide, calcium oxide, strontium oxide, barium oxide, titanium dioxide, and silicon dioxide.

2. An oxygen gas permselective membrane according to claim 1, wherein said film has a thickness of about 0.01 to about 1.0 $\mu$m.

3. An oxygen gas permselective membrane according to claim 1, wherein said film is deposited integrally on either surface of a porous membrane of 0.1 $\mu$m or less in pore size.

4. An oxygen gas permselective membrane according to claim 3, wherein said film has a thickness of about 0.01 to about 1.0 $\mu$m.

5. An oxygen gas permselective membrane according to claim 3, wherein a water repellent layer is interposed integrally and laminatedly between said film and said porous membrane.

6. An oxygen gas permselective membrane according to claim 5, wherein said water repellent layer comprises a thin layer obtained by plasma polymerization of a monomolecular fluorinated organic compound.

7. An oxygen gas permselective membrane according to claim 5, wherein said water repellent layer and said film of the metallic oxide each have a thickness within the range of about 0.01 to about 1.0 $\mu$m.

8. An oxygen gas permselective membrane according to claim 1, further comprising a porous electrode body defining a gas-side surface to which one of the group consisting of said film and said porous membrane is applied, said porous electrode body having an electrochemical reducing function relative to oxygen gas and simultaneously a current collecting function.

9. An oxygen gas permselective membrane according to claim 8, wherein said metallic oxide is deposited on the gas-side surface of the electrode body by means of a deposition process or sputtering process.

10. An oxygen gas permselective membrane according to claim 8, which is prepared by a process comprising the steps of (i) depositing said film consisting essentially of said metallic oxide on a surface of a porous membrane having pores in the size range of about 0.1 $\mu$m or less; and thereafter (ii) integrally and compressedly bonding said porous membrane to said gas-side surface of said electrode body.

11. An oxygen gas permselective membrane according to claim 10, wherein a water repellent layer is interposed integrally and laminatedly between said film and said porous membrane.

12. An oxygen gas permselective membrane according to claim 11, wherein said water repellent layer comprises a thin layer obtained by plasma polymerization of a monomolecular fluorinated organic compound.

13. An oxygen gas permselective membrane according to claim 11, wherein said water repellent layer and said film of the metallic oxide each have a thickness within the range of about 0.01 to about 1.0 μm.

* * * * *